United States Patent
Vanderpool et al.

(10) Patent No.: US 12,383,305 B2
(45) Date of Patent: *Aug. 12, 2025

(54) SUBCUTANEOUS DELIVERY TOOL

(71) Applicant: Medtronic, Inc., Minneapolis, MN (US)

(72) Inventors: Matthew T. Vanderpool, Fridley, MN (US); Michael R. Klardie, Plymouth, MN (US); Kris A. Peterson, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/482,428

(22) Filed: Oct. 6, 2023

(65) Prior Publication Data
US 2024/0032963 A1 Feb. 1, 2024

Related U.S. Application Data

(60) Continuation of application No. 17/165,304, filed on Feb. 2, 2021, now Pat. No. 11,779,370, which is a
(Continued)

(51) Int. Cl.
*A61B 17/34* (2006.01)
*A61B 5/29* (2021.01)
(Continued)

(52) U.S. Cl.
CPC ............ *A61B 17/3468* (2013.01); *A61B 5/29* (2021.01); *A61B 17/32093* (2013.01);
(Continued)

(58) Field of Classification Search
CPC . A61B 17/3468; A61B 5/29; A61B 17/32093; A61B 5/283;
(Continued)

(56) References Cited

U.S. PATENT DOCUMENTS

| 2,009,393 A | 7/1935 | Gioacchino |
| 2,647,512 A | 8/1953 | Johnson |

(Continued)

FOREIGN PATENT DOCUMENTS

| CN | 1031481 A | 3/1989 |
| CN | 2621634 Y | 6/2004 |

(Continued)

OTHER PUBLICATIONS

Communication pursuant to Article 94(3) EPC (examination report) from counterpart European Patent Application No. 14717919.6 dated Jul. 28, 2017, 5 pp.

(Continued)

*Primary Examiner* — Jing Rui Ou
(74) *Attorney, Agent, or Firm* — Shumaker & Sieffert, P.A.

(57) ABSTRACT

Subcutaneous implantation tools and methods of implanting a subcutaneous device using the same. The tool may include a tool body having a longitudinally extending recess having a distal opening and having a tunneler at a distal end of the tool body extending from the distal opening of the recess. The tool may include a plunger slidably fitting within at least a portion of the tool body recess. The recess may be configured to receive an implantable device and the tunneler preferably extends distally from the recess at a position laterally displaced from the device when the device is so located in the recess. Movement of the plunger distally within the recess advances the device distally out of the recess and alongside of and exterior to the tunneler.

19 Claims, 9 Drawing Sheets

Related U.S. Application Data division of application No. 17/000,688, filed on Aug. 24, 2020, now Pat. No. 11,857,218, which is a continuation of application No. 15/610,076, filed on May 31, 2017, now Pat. No. 10,786,279, which is a continuation of application No. 14/204,227, filed on Mar. 11, 2014, now Pat. No. 11,311,312.

(60) Provisional application No. 61/788,940, filed on Mar. 15, 2013.

(51) Int. Cl.
| | |
|---|---|
| *A61B 17/3209* | (2006.01) |
| *A61B 5/283* | (2021.01) |
| *A61B 17/32* | (2006.01) |
| *A61N 1/372* | (2006.01) |
| *A61N 1/375* | (2006.01) |

(52) U.S. Cl.
CPC ... *A61B 5/283* (2021.01); *A61B 2017/320044* (2013.01); *A61B 2017/320056* (2013.01); *A61N 1/37205* (2013.01); *A61N 1/3756* (2013.01)

(58) Field of Classification Search
CPC ....... A61B 2017/320044; A61B 2017/320056; A61N 1/37205; A61N 1/3756
See application file for complete search history.

(56) References Cited

U.S. PATENT DOCUMENTS

| | | | |
|---|---|---|---|
| 3,744,493 A | 7/1973 | Booher et al. | |
| 4,915,686 A | 4/1990 | Frederick | |
| 5,127,404 A | 7/1992 | Wyborny et al. | |
| 5,304,119 A | 4/1994 | Balaban et al. | |
| 5,484,403 A | 1/1996 | Yoakum et al. | |
| 5,507,807 A | 4/1996 | Shippert | |
| 5,562,613 A | 10/1996 | Kaldany | |
| 5,772,671 A | 6/1998 | Harmon | |
| 5,842,999 A | 12/1998 | Pruitt et al. | |
| 5,954,670 A | 9/1999 | Baker | |
| 5,987,352 A | 11/1999 | Klein et al. | |
| 6,230,059 B1 | 5/2001 | Duffin | |
| 6,317,626 B1* | 11/2001 | Warman | A61N 1/3702 607/59 |
| 6,412,490 B1 | 7/2002 | Lee | |
| 7,035,684 B2 | 4/2006 | Lee | |
| 8,888,745 B2 | 11/2014 | Van Der Graaf et al. | |
| 10,786,279 B2* | 9/2020 | Vanderpool | A61B 5/29 |
| 11,134,985 B2* | 10/2021 | Vanderpool | A61B 17/3468 |
| 11,134,986 B2* | 10/2021 | Vanderpool | A61B 5/29 |
| 11,154,323 B2* | 10/2021 | Vanderpool | A61B 5/29 |
| 11,241,253 B2* | 2/2022 | Vanderpool | A61B 5/29 |
| 11,311,312 B2* | 4/2022 | Vanderpool | A61B 17/32093 |
| D976,397 S | 1/2023 | Vanderpool et al. | |
| D979,752 S | 2/2023 | Vanderpool et al. | |
| 11,779,370 B2* | 10/2023 | Vanderpool | A61B 17/3468 606/190 |
| D1,006,990 S | 12/2023 | Vanderpool et al. | |
| 11,857,218 B2* | 1/2024 | Vanderpool | A61B 17/32093 |
| 2001/0029386 A1 | 10/2001 | Matsutani et al. | |
| 2003/0088212 A1 | 5/2003 | Tal | |
| 2003/0200665 A1* | 10/2003 | Li | B25G 1/102 30/329 |
| 2004/0082969 A1 | 4/2004 | Kerr | |
| 2004/0143284 A1 | 7/2004 | Chin | |
| 2004/0193154 A1 | 9/2004 | Leatherbury et al. | |
| 2004/0249388 A1 | 12/2004 | Michelson | |
| 2005/0090852 A1 | 4/2005 | Layne et al. | |
| 2005/0096645 A1 | 5/2005 | Wellman et al. | |
| 2005/0107768 A1 | 5/2005 | Ting | |
| 2006/0074434 A1 | 4/2006 | Wenstrom, Jr. et al. | |
| 2006/0097331 A1 | 5/2006 | Hattori et al. | |
| 2006/0106415 A1 | 5/2006 | Gabbay | |
| 2006/0174898 A1 | 8/2006 | Brown | |
| 2007/0010738 A1 | 1/2007 | Mark et al. | |
| 2007/0179515 A1 | 8/2007 | Matsutani et al. | |
| 2007/0249992 A1 | 10/2007 | Bardy | |
| 2008/0110033 A1* | 5/2008 | Peterson | B26B 5/00 30/329 |
| 2008/0154298 A1 | 6/2008 | Grayzel et al. | |
| 2009/0030426 A1 | 1/2009 | Zinn et al. | |
| 2009/0036917 A1 | 2/2009 | Anderson | |
| 2009/0137946 A1 | 5/2009 | Nassiri et al. | |
| 2010/0030227 A1 | 2/2010 | Kast et al. | |
| 2010/0094252 A1 | 4/2010 | Wengreen et al. | |
| 2010/0198140 A1 | 8/2010 | Lawson | |
| 2010/0268258 A1* | 10/2010 | Maxwell | A61B 17/3213 606/167 |
| 2010/0324578 A1 | 12/2010 | Bardy | |
| 2010/0331868 A1 | 12/2010 | Bardy | |
| 2011/0034886 A1 | 2/2011 | Elbe et al. | |
| 2012/0283705 A1 | 11/2012 | Lee et al. | |
| 2014/0128963 A1 | 5/2014 | Quill et al. | |
| 2016/0175007 A1 | 6/2016 | Valbuena et al. | |
| 2020/0129206 A1 | 4/2020 | Cornelius et al. | |

FOREIGN PATENT DOCUMENTS

| | | |
|---|---|---|
| CN | 2702718 Y | 6/2005 |
| CN | 202342097 U | 7/2012 |
| DE | 469951 C | 1/1929 |
| DE | 4243641 A1 | 9/1994 |
| EP | 3034128 A1 | 6/2016 |
| JP | 2001502937 A | 3/2001 |
| JP | 2007516031 A | 6/2007 |
| JP | 2008528084 A | 7/2008 |
| JP | 2011092065 A | 5/2011 |
| WO | 9813091 A1 | 4/1998 |
| WO | 2005044116 A2 | 5/2005 |
| WO | 2005060306 A1 | 6/2005 |
| WO | 2008016551 A1 | 2/2008 |
| WO | 2009018008 A2 | 2/2009 |
| WO | 2012098356 A1 | 7/2012 |

OTHER PUBLICATIONS

Communication pursuant to Article 94(3) EPC from counterpart European Application No. 18188908.0 dated Feb. 3, 2022, 5 pp.

Communication Pursuant to Rules 161(1) and 162 EPC from counterpart European Application No. 14717919.6, dated Nov. 4, 2015, 2 pp.

Decision on Reexamination from counterpart Chinese Application No. 201480015082.5, dated Sep. 11, 2019, 11 pp.

Decision to Grant and translation thereof, from counterpart Japanese Application No. 2016-501382, dated Jun. 26, 2018, 5 pp.

Decision to Grant from counterpart European Application No. 14717919.6, dated Jun. 9, 2018, 1 pp.

Examination Report from counterpart European Application No. 14717919.6, dated Jul. 28, 2017, 5 pp.

Examination Report from counterpart European Application No. 18188908.0, dated May 26, 2021, 7 pp.

Extended European Search Report from counterpart European Patent Application No. 18188908.0, dated Oct. 19, 2018, 7 pp.

First Office Action and Search Report, and translation thereof, from counterpart Chinese Application No. 201480015082.5, dated Mar. 20, 2017, 18 pp.

Fourth Office Action, and translation thereof, from counterpart Chinese Application No. 201480015082.5, dated Jun. 22, 2020, 13 pp.

Intent to Grant from counterpart European Application No. 14717919.6, dated Apr. 16, 2018, 30 pp.

International Preliminary Report on Patentability from International Application number PCT/US2014/023912, mailed Sep. 15, 2015, 5 pp.

International Search Report and the Written Opinion from International Application number PCT/US2014/023912, mailed Jun. 20, 2014, 9 pp.

(56) References Cited

OTHER PUBLICATIONS

Notice of Intent to Grant and Text Intended to Grant from counterpart European Application No. 18188908.0 dated Mar. 15, 2023, 36 pp.
Notice of Reasons for Refusal and translation thereof, from counterpart Japanese Application No. 2018-137778, dated Jun. 25, 2019, 15 pp.
Notice of Reasons for Refusal, and translation thereof, from counterpart Japanese Application No. 2018-137778, dated Jun. 28, 2019, 12 pp.
Notice on the Second Office Action, and translation thereof, from counterpart Chinese Application No. 201480015082.5, dated Mar. 5, 2018, 9 pp.
Office Action, and translation thereof, from counterpart Japanese Application No. 2018137778, dated Feb. 6, 2020, 3 pp.
Office Action, and translation thereof, from counterpart Japanese Patent Application No. 2016-501382, dated Oct. 29, 2017, 7 pp.
Preliminary Amendments filed in counterpart European Patent Application No. 14717919.6, filed on Oct. 9, 2015, 9 pp.
Prosecution History from U.S. Appl. No. 14/204,227, now issued U.S. Pat. No. 11,311,312, dated Apr. 28, 2014 through Mar. 24, 2022, 554 pp.
Prosecution History from U.S. Appl. No. 15/610,076, now issued U.S. Pat. No. 10,786,279, dated Jun. 8, 2017 through Aug. 3, 2020, 235 pp.
Prosecution History from U.S. Appl. No. 17/000,688, now issued U.S. Pat. No. 11,857,218, dated Dec. 8, 2022 through Aug. 23, 2023, 50 pp.
Prosecution History from U.S. Appl. No. 17/165,304, now issued U.S. Pat. No. 11,779,370, dated Feb. 2, 2023 through Sep. 8, 2023, 43 pp.
Prosecution History from U.S. Appl. No. 17/323,298, dated Sep. 9, 2021, 16 pp.
Prosecution History from U.S. Appl. No. 17/325,873, dated Sep. 3, 2021, 14 pp.
Prosecution History from U.S. Appl. No. 17/325,904, now issued U.S. Pat. No. 11,134,986, dated Aug. 11, 2021 through Sep. 10, 2021, 28 pp.
Prosecution History from U.S. Appl. No. 17/329,986, now issued U.S. Pat. No. 11,241,253, dated Sep. 30, 2021 through Dec. 15, 2021, 32 pp.
Response to Communication Pursuant to Rule 69 EPC dated Jan. 7, 2019 and the Extended European Search Report dated Oct. 19, 2018, from counterpart European Application No. 18188908.0, filed Apr. 15, 2019, 13 pp.
U.S. Appl. No. 29/748,588, filed Aug. 31, 2020, naming inventors Vanderpool et al.
Response to Communication pursuant to Rules 161(1) dated Nov. 4, 2015 from counterpart European Patent Application No. 14717919.6, filed on May 13, 2016, 5 pp.
Response to Examination Report dated Feb. 3, 2022, from counterpart European Application No. 18188908.0, filed May 16, 2022, 22 pp.
Response to Examination Report dated Jul. 28, 2017, from counterpart European Application No. 14717919.6, filed Dec. 6, 2017, 13 pp.
Response to Examination Report from counterpart European Application No. 18188908.0, dated May 26, 2021, filed Sep. 30, 2021, 24 pp.
Response to the Communication pursuant to Article 94(3) EPC (examination report), dated Jul. 28, 2017, from counterpart European Patent Application No. 14717919.6, filed Dec. 6, 2017, 13 pp.
Response to the Communication pursuant to Rule 69 EPC of Jan. 7, 2019 and the Extended Search Report forwarded on Oct. 19, 2018, from counterpart European Application No. 18188908.0, filed Apr. 15, 2019, 13 pp.
The Decision on Rejection, and translation thereof, from counterpart Chinese Application No. 201480015082.5, dated Dec. 5, 2018, 14 pp.
Decision on Rejection, and translation thereof, from counterpart Chinese Application No. 201480015082.5, dated Sep. 11, 2019, 11 pp.
The Notification of Rejection, and translation thereof, from counterpart Chinese Application No. 2014-80015082.5, dated Nov. 4, 2020, 11 pp.
Third Office Action, and translation thereof, from counterpart Chinese Application No. 201480015082.5, dated Apr. 7, 2020, 13 pp.
U.S. Appl. No. 18/488,368, filed Oct. 17, 2023, naming inventors Vanderpool et al.
Extended Search Report from counterpart European Application No. 18188908.0 dated Mar. 15, 2024, 7 pp.
Office Action from U.S. Appl. No. 18/488,368 dated May 22, 2024, 28 pp.
Response to Office Action dated May 22, 2024 from U.S. Appl. No. 18/488,368, filed Aug. 21, 2024, 12 pp.
Advisory Action from U.S. Appl. No. 18/488,368 dated Feb. 6, 2025, 3pp.
Final Office Action from U.S. Appl. No. 18/488,368 dated Nov. 29, 2024, 25 pp.
Response to Final Office Action dated Nov. 29, 2024 from U.S. Appl. No. 18/488,368, filed Jan. 29, 2025, 10 pp.
Office Action from U.S. Appl. No. 18/488,368 dated Mar. 12, 2025, 21 pp.
Final Office Action from U.S. Appl. No. 18/488,368 dated Jun. 17, 2025, 20 pp.
Response to Office Action dated Mar. 12, 2025 from U.S. Appl. No. 18/488,368, filed Jun. 5, 2025, 9 pp.

\* cited by examiner

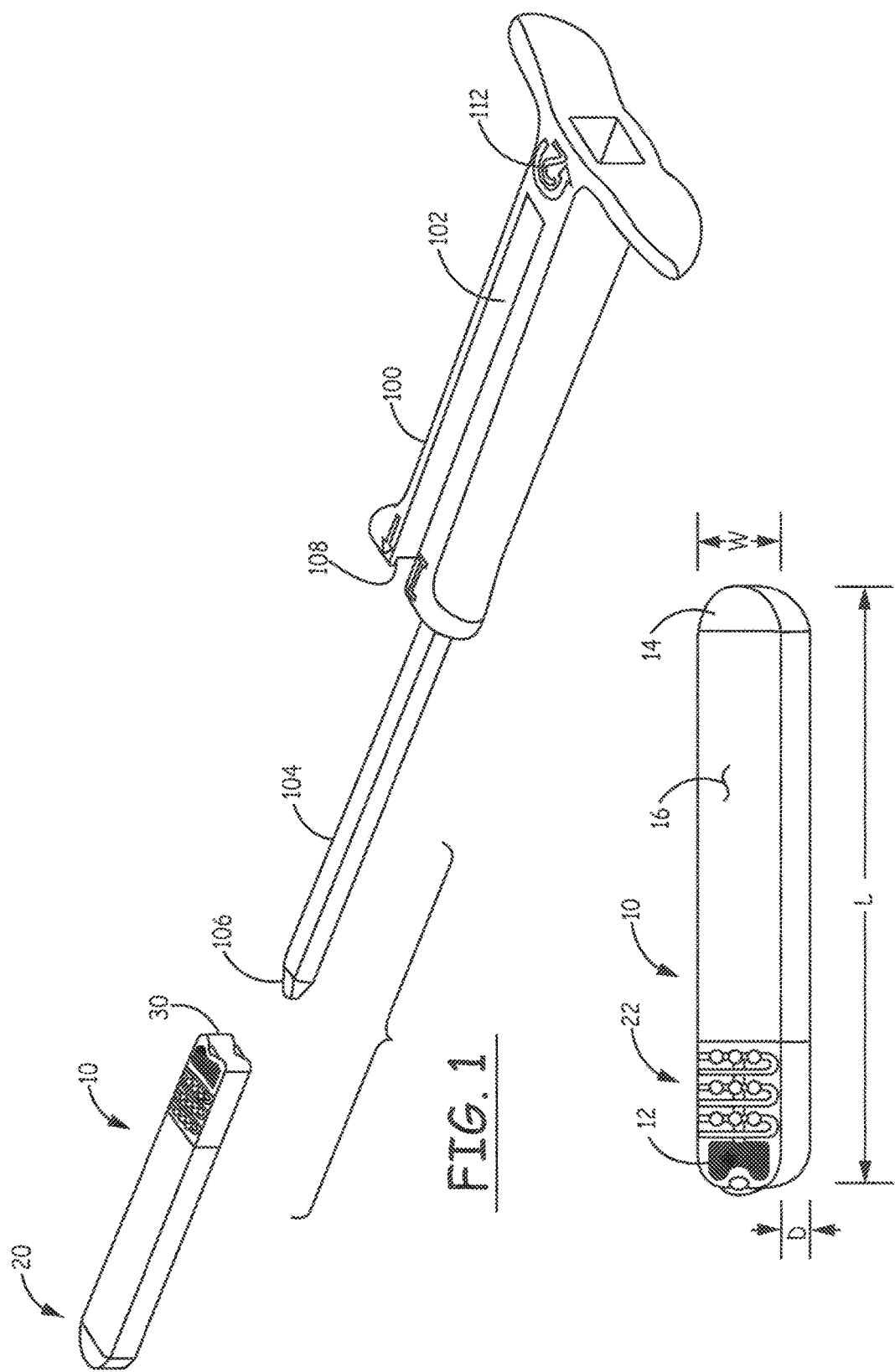

SUBCUTANEOUS DELIVERY TOOL

This application is a continuation of U.S. patent application Ser. No. 17/165,304, filed Feb. 2, 2021, which is a divisional of U.S. patent application Ser. No. 17/000,688, filed Aug. 24, 2020, which is a continuation of U.S. patent application Ser. No. 15/610,076, filed May 31, 2017 (now U.S. Pat. No. 10,786,279, issued Sep. 29, 2020), which is a continuation of U.S. patent application Ser. No. 14/204,227, filed Mar. 11, 2014 (now U.S. Pat. No. 11,311,312, issued Apr. 26, 2022), which claims the benefit of U.S. Provisional Application No. 61/788,940, filed Mar. 15, 2013. The entire content of each of these applications is incorporated herein by reference.

BACKGROUND

The use of monitoring equipment to measure various physical parameters of a patient is well known. There is a growing demand for using subcutaneous monitoring devices, which allow doctors to obtain information without a patient being connected to an external machine and/or which may otherwise not be reproducible in office settings. The term subcutaneous generally implies locations within the body of a patient under the skin and exterior to the musculature beneath the skin. For example, an implantable device that includes the ability to monitor a patient's heart beat in order to detect transient symptoms suggesting cardiac arrhythmia allows doctors to review data over a longer period of time than using external monitoring equipment in a simulated testing situation. However, to successfully implant implantable subcutaneous devices an implantation tool should, for example, ensure that the device is not implanted in muscle, reduce contact between the surgeon and the wound, be used in an office setting to minimize patient discomfort and the need for invasive surgery and have the ability to repeatedly recreate the same size incision site in the patient.

Exemplary prior art insertion tools include those illustrated in US Patent Application Publication No. 2010/0094252 by Wengreen, et al., incorporated herein by reference in its entirety.

SUMMARY

Further areas of applicability will become apparent from the description provided herein. It should be understood that the description and specific examples are intended for purposes of illustration only and are not intended to limit the scope of the present disclosure.

Exemplary embodiments provide subcutaneous implantation tools and methods of implanting a subcutaneous micro-device using the same. The invention provides a syringe-like tool, comprising a tool body, hereafter "handle", having a hollow, distally longitudinally extending recess such as a bore or channel and having a distal opening through which the device may be delivered. The device preferably also includes a movable plunger located within the bore or channel. An incision tool is provided to make an incision through which the subcutaneous device is implanted.

The device may, for example, be implanted in the region of the thorax. A specific recommended location will typically be provided within an associated product manual. In one embodiment, two electrodes on the body of the device monitor the patient's subcutaneous ECG. The device may ECG recordings in response to patient activation or in response to automatically detected arrhythmias. Exemplary devices are disclosed in US Patent Application Publication No. 2009/0036917 by Anderson, US Patent Application Publication No. 2010/0094252 by Wengreen, et al., US Patent Application Publication No. 2012/0283705 by Hoeppner, et al., U.S. Pat. No. 5,987,352, issued to Klein, et al., U.S. Pat. Nos. 6,412,490 and 7,035,684 issued to Lee, et al. and U.S. Pat. No. 6,230,059, issued to Duffin, et al., all incorporated herein by reference in their entireties.

The incision tool is designed to create an incision of repeatable width and depth with a single motion. It is composed of a blade, designed to make a repeatable incision, and handle, designed to ergonomically fit the hand. The incision tool is intended to make the incision simple and repeatable. Other mechanisms for making openings in the patient's skin such as trocars, spreaders, scalpels and the like may be substituted in some alternative embodiments. The insertion tool delivers the device through the incision and into the subcutaneous tissue. The tool is designed to ensure the device is delivered into a tight pocket to maximize electrode contact with the surrounding tissue in a highly repeatable manner, and is composed of two parts: a handle and a plunger. The handle is composed of a bore or channel section, used to hold the device and guide it during implant, and a protrusion extending distally of the channel, used to bluntly dissect an implant path for the device to travel down while being implanted. The tunneler extends distally from the channel a position laterally displaced from the device when the device is located in the channel. The plunger is used to push the device distally out of the handle, through the incision, alongside and exterior to the tunneler and along the implant path created by the tunneler to the final implant location.

The device is typically loaded into the channel section of the insertion tool handle and sterile packaged along with both the insertion tool plunger and the incision tool.

The device is locatable within the channel distal to the plunger, so that when the plunger is moved distally, the device advances distally out of the tool body and into the tissue. Typically, the device will take the form of an elongated body, having a length greater than its thickness and width, as illustrated in the published Application No. 2010/0094252, cited above. The device may extend along its longitudinal axis between proximal and distal ends. The longitudinal channel or bore of the tool body may conform at least in part to the outer configuration of the device and more typically to a cross section of the device taken along its longitudinal axis. If the device, like the above discussed device, has a width greater than its depth and/or is otherwise radially asymmetric around its longitudinal axis, this feature allows the device to be advanced into the tissue while maintaining a desired orientation, as discussed in more detail below.

Optimally, the final insertion site of the device is located a short distance from the incision site. As noted above, the handle is preferably provided with an elongated protrusion or tunneler extending distally from the distal opening of the bore, which is insertable into the tissue through the incision to create a path in the tissue, along which the device may be advanced when pushed by the plunger. The distal end of the tunneler when so inserted is preferably located at the desired location of the distal end of the device. The length of the tunneler is thus preferably at least equal to and preferably somewhat greater than the length of the subcutaneous device.

Additional embodiments provide methods of implanting a subcutaneous micro-device, including inserting the dissection body of the tool described by the embodiments of the tool into an implantation site, where the dissection body includes a micro-device, and delivering the micro-device.

BRIEF DESCRIPTION OF DRAWINGS

Exemplary embodiments will be more clearly understood from the following detailed description taken in conjunction with the accompanying drawings. FIGS. 1-10 represent non-limiting, example embodiments as described herein.

FIG. 1 is a perspective view of an exemplary implantable device and the associated tool handle.

FIG. 2 is a perspective view of the exemplary implantable device.

FIG. 3 is a perspective view of the incision tool according to exemplary embodiments.

FIG. 10 is a flow chart illustrating a method of delivering a device to a subcutaneous site according to exemplary embodiments.

DETAILED DESCRIPTION

Figure 3:
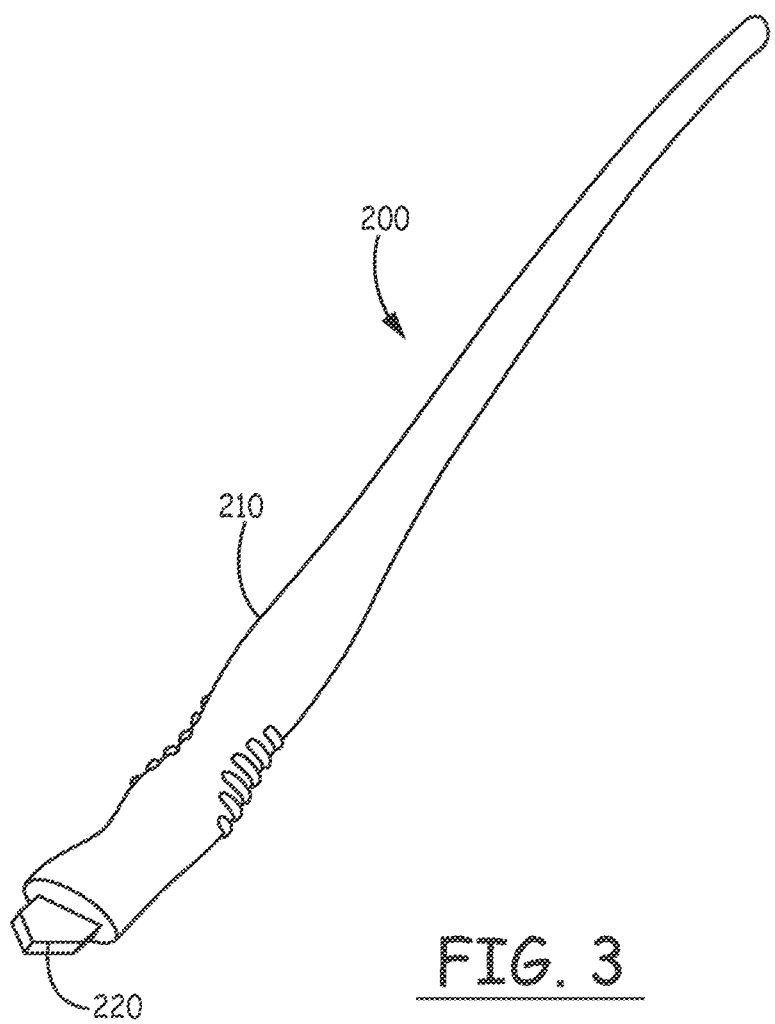

Various exemplary embodiments will now be described more fully with reference to the accompanying drawings in which some exemplary embodiments are illustrated. In the drawings, the thicknesses of layers and regions may be exaggerated for clarity.

Accordingly, while exemplary embodiments are capable of various modifications and alternative forms, embodiments thereof are shown by way of example in the drawings and will herein be described in detail. It should be understood, however, that there is no intent to limit exemplary embodiments to the particular forms disclosed, but on the contrary, exemplary embodiments are to cover all modifications, equivalents, and alternatives falling within the scope of the invention Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of exemplary embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing only particular embodiments and is not intended to be limiting of exemplary embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, e.g., "beneath," "below," "lower," "above," "upper" and the like, may be used herein for ease of description to describe one element or a relationship between a feature and another element or feature as illustrated in the figures. It will be understood that the spatially relative terms are intended to encompass different orientations of the device in use or operation in addition to the orientation depicted in the Figures. For example, if the device in the figures is turned over, elements described as "below" or "beneath" other elements or features would then be oriented "above" the other elements or features. Thus, for example, the term "below" can encompass both an orientation which is above as well as below. The device may be otherwise oriented (rotated 90 degrees or viewed or referenced at other orientations) and the spatially relative descriptors used herein should be interpreted accordingly.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which exemplary embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Exemplary embodiments are directed to subcutaneous implantation tools and methods of implanting subcutaneous micro-devices. FIGS. 1A to 10 illustrate various exemplary embodiments of such subcutaneous implantation tools.

FIG. 1 shows the implantable device 10, aligned longitudinally with the handle 100, arranged for the insertion of device 10 into the channel 102 of the handle 100. The proximal end 20 of the device is inserted into the distal end 108 of the channel 102 of the handle and is advanced proximally until the proximal end 30 of the device is located adjacent an internal stop surface (not illustrated) within the handle 100. At this point, the distal end 20 of the device will be adjacent the distal end 108 of the handle 100. The open upper portion of the channel 102 allows visual verification that the device 10 is properly inserted into the channel. The tunneler 104 extends distally of the distal end 108 of channel 102. The distal end 106 of the tunneler is placed into the incision made by the incision tool with its upper surface facing outward of the patient's body and advanced to provide blunt dissection of the subcutaneous tissue to a point where the distal end 20 of the device is adjacent the opening of the incision. The handle 100 is then rotated 180 degrees so that the tunneler 104 is then above the device (outward relative to the patient's skin). This allows upward pressure on the handle to assist in temporarily enlarging the incision and assures that the device will not escape as advanced distally into the tissue. The device 10 is then advanced by distal movement of the plunger illustrated in FIG. 5B within the channel 102 and along the tunneler 104 until it is properly located within the tissue, displaced distally a short distance from the opening of the incision. The logo 112 assists in reminding the physician to rotate the handle prior to insertion of the plunger and advancement of the device.

FIG. 2 shows the device 10 in more detail. In this view it can be seen that the device comprises two electrodes 12 and 14, located adjacent the proximal and distal ends, respectively, of the device. When implanted, electrode 12, located on the upper surface 16 of the device preferably faces outward toward the skin. As such, when the device is placed into the handle as discussed above, the electrode 12 faces downward and is not visible through the open upper portion of the channel, allowing verification of proper insertion into the handle.

The exemplary device 10 as illustrated generally takes the form of an elongated rectangular prism having rounded corners and a rounded distal end portion. The rounded distal end of the device assists in allowing it to advance into body tissue, providing blunt dissection of the tissue as it advances. Because the cross section of the device is substantially greater than the cross section of the tunneler, the device will be located snugly within the tissue, reducing the chances for the formation of air bubbles adjacent the electrodes and also assisting in maintaining the device in its desired position. The device has length (L), width (W) and depth (D) as illustrated. In this particular embodiment, the with is greater than the depth, providing radial asymmetry along the longitudinal axis of the device and assisting in maintaining the device in its proper orientation with upper surface 16 facing outward after implant. A suture hole 18 may optionally be provided at the proximal end of the device to allow the physician to suture it to underlying tissue if desired. Projections 22 may optionally be provided to prevent longitudinal movement of the device after implant.

As discussed above, the inner surface of the channel of the handle is preferably configured to correspond to the outer configuration of the device. As discussed below in more detail, the configuration of the channel of the handle is configured to engage the rounded corners of the device, preventing rotation of the device within the handle.

FIG. 3 illustrates the incision tool 200, which is provided with a curved plastic handle 210 fitted with a flat, pointed blade 220 having a width equal to the desired width of the incision. The handle is designed to be comfortably held in a position allowing the blade to be advanced through the skin at a shallow angle, avoiding damage to underlying muscle tissue.

Figure 4A:
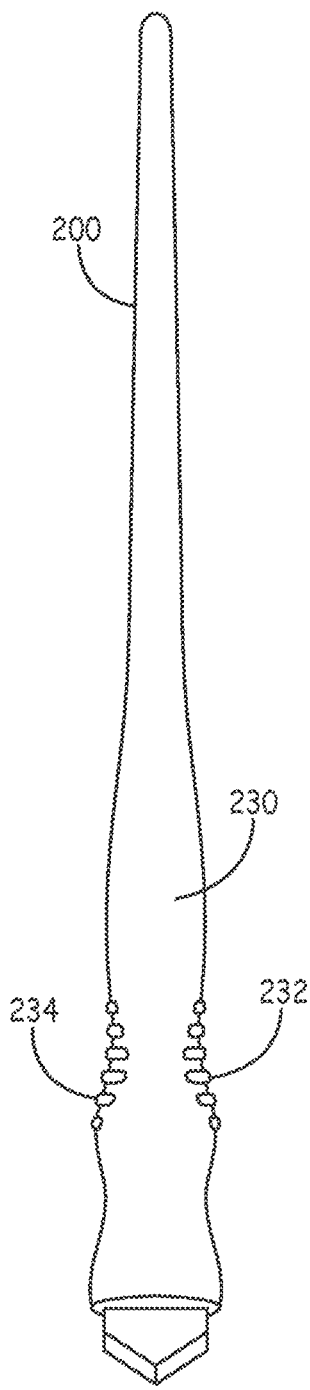
FIGS. 4A, 4B and 4C are top, side and bottom views, respectively, of the incision tool of FIG. 3.
Figure 4B:
Figure 4C:

FIGS. 4A, 4B and 4C show top, side and bottom views of the incision device 200. As illustrated in 4A, both the differing coloration of the finger grips 234 and 232 and the placement of the logo 236 on the upper surface assist the physician in assuring that the orientation of the blade is correct to provide the desired shallow penetration angle.

Figure 5A:
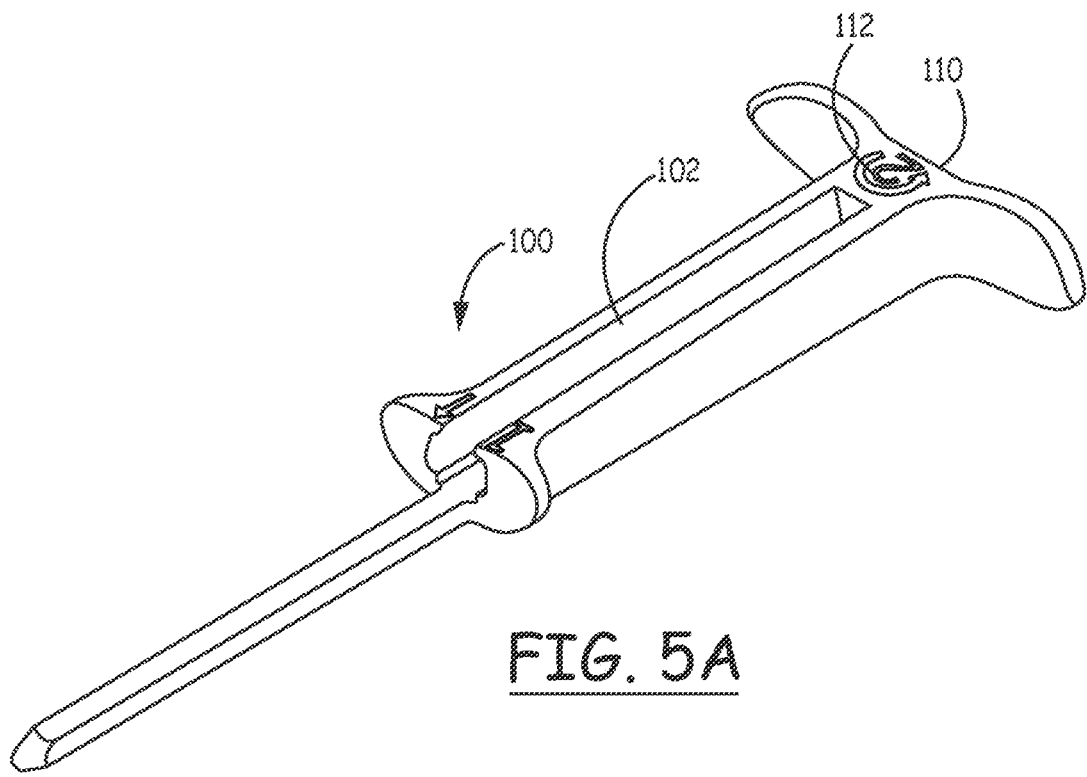
FIGS. 5A and 5B are perspective views of the tool handle and plunger, respectively, according to exemplary embodiments of the invention.
Figure 5B:
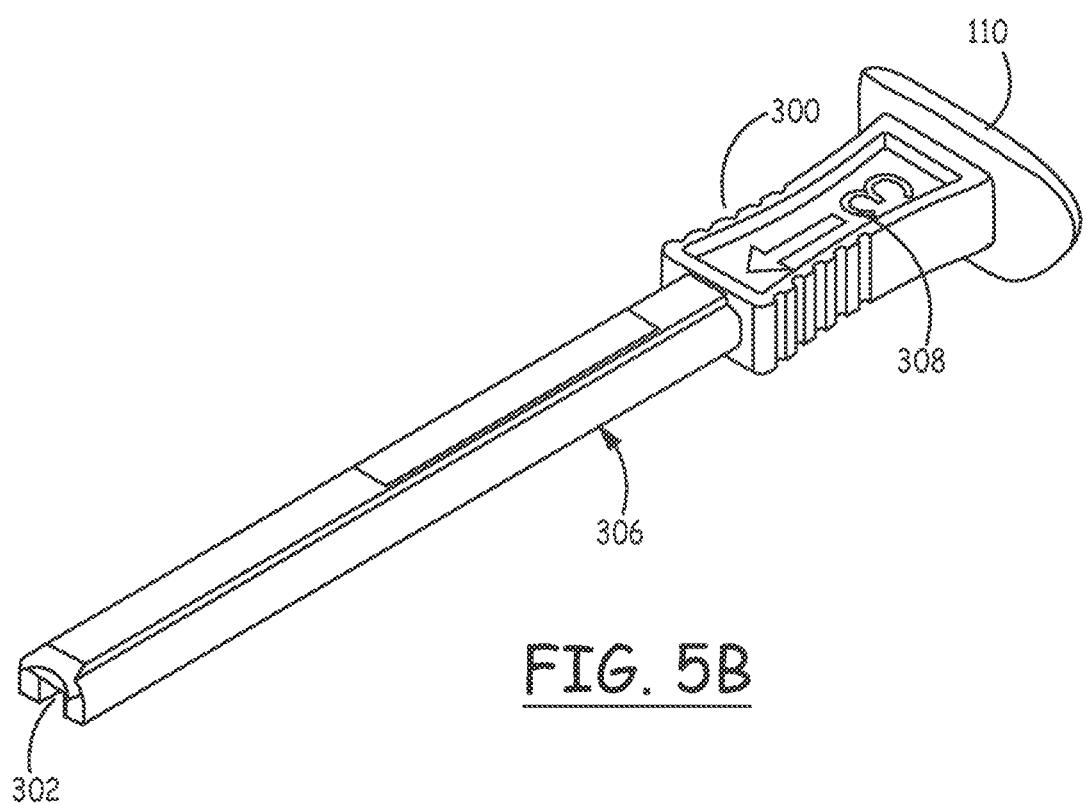

FIGS. 5A and 5B show the handle 100 and the plunger 300 prior to insertion of the plunger into the handle. After rotation of the handle so that its upper surface bearing marking 112 now faces inward toward the patient's skin, the distal end 302 of plunger 300 is then inserted into an opening in the proximal end 110 of the handle and into the channel 102 of the handle.

The plunger is provided with a groove 306 running the length of the lower surface of the plunger up to a distal stop surface discussed below. The opening in the proximal end of the handle includes a protrusion corresponding to the groove in the lower surface of the plunger, assuring its proper orientation within the handle. A marking 308 adjacent the proximal end of the plunger assists the physician in determining that the plunger is in the proper orientation for insertion into the handle.

The plunger is advanced distally, pushing the device into the incision along the then inward facing surface of the tunneler. The device thus follows the path defined by the tunneler to assure proper placement within the tissue. After insertion of the device, the handle and plunger are removed.

Various medical grade materials may be used to form the various parts of the subcutaneous implantation tool, for example, plastics, metals, rubber, sanitizable materials, etc. Exemplary embodiments of the subcutaneous implantation tool may be inexpensive, disposable, etc. The subcutaneous implantation tool may also be configured to be used with known automated injection systems, which use, e.g., compressed air or other inert gases in place of a manual plunger.

FIGS. 6A, 6B, 6C, 6D and 6E are distal end, cut-away, top, bottom and proximal end views, respectively, of the tool handle 100. In these views the projection 114 is visible. Projection 114 provides a distal facing stop surface limiting the insertion of the device 10 into the channel 102. It further engages the slot in the lower surface of the plunger 300, assuring proper orientation of the plunger within the handle. It also provides a proximal facing stop surface limiting distal movement of the plunger. The handle is also show as optionally provided with a slot 116 in its lower surface, through which advancement of the plunger and device can be observed.

Figure 6A:
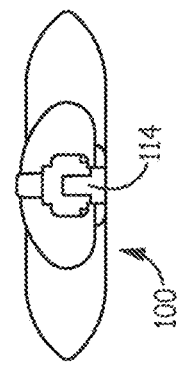
FIGS. 6A, 6B, 6C, 6D and 6E are distal end, cut-away, top, bottom and proximal end views, respectively, of the tool handle.
Figure 6E:
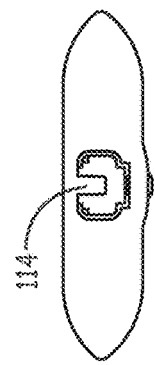
Figure 6D:
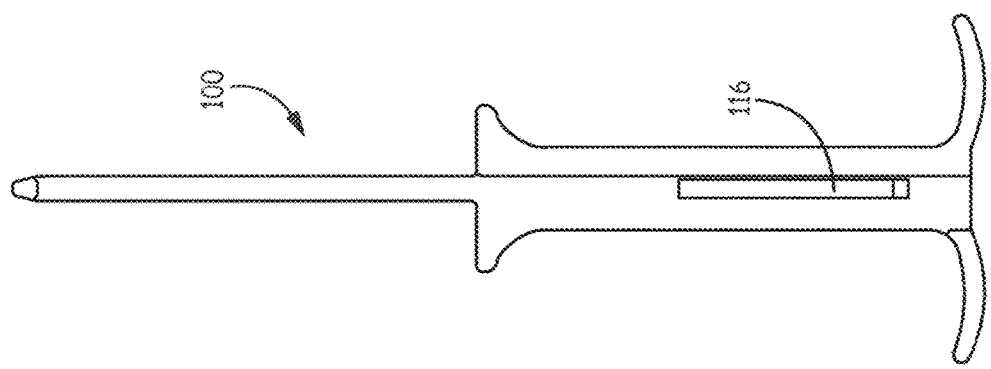
Figures 6B, 6C:
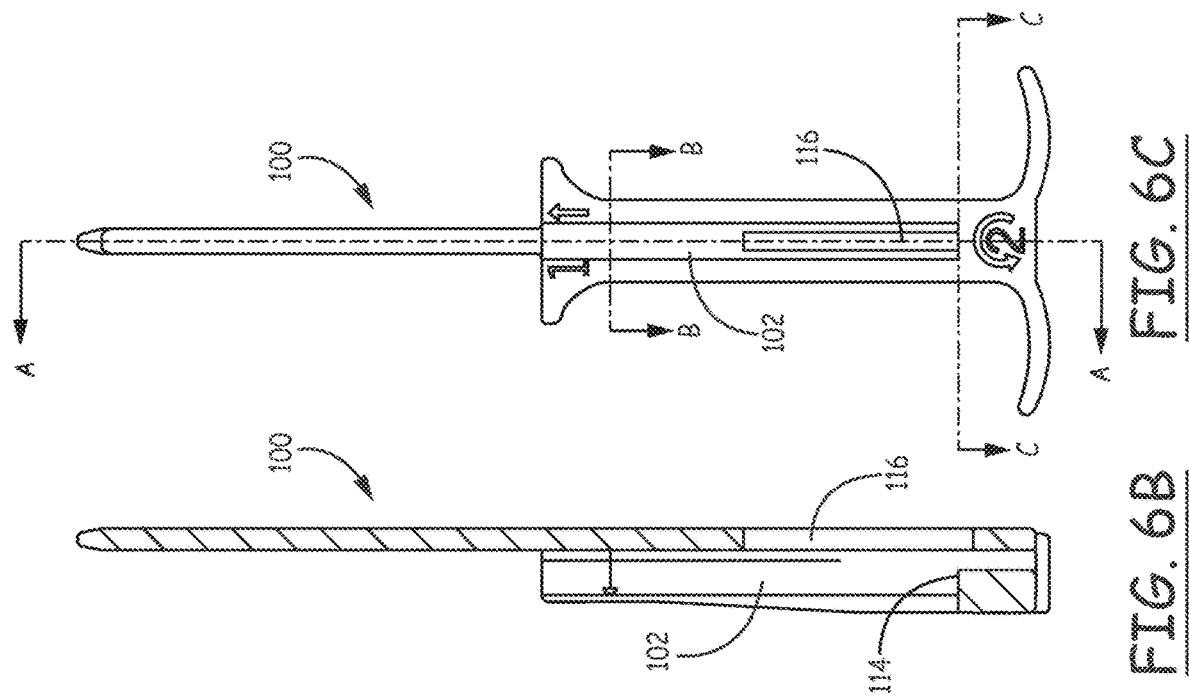
Figure 7A:
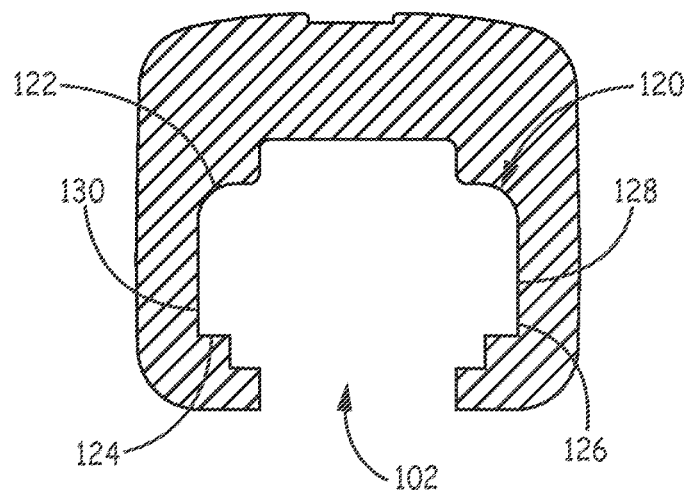
FIGS. 7A and 7B are cross sectional views through the tool handle as illustrated in FIG. 6C.
Figure 7B:
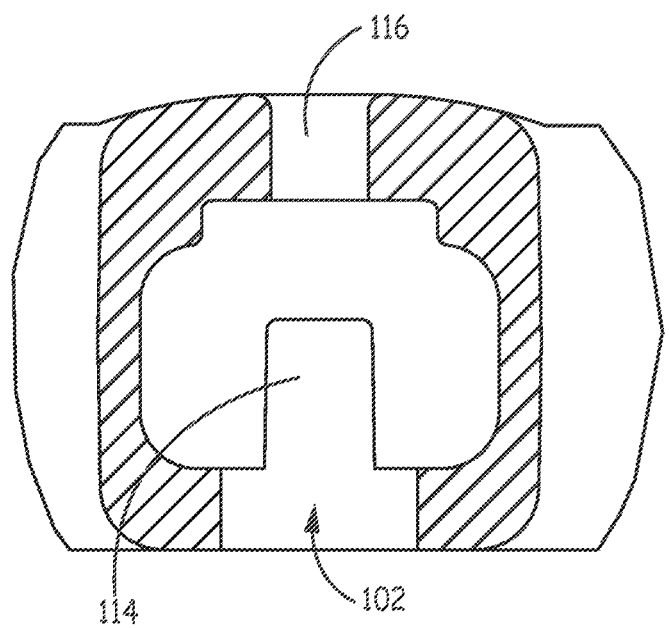

FIGS. 7A and 7B are cross sectional views through the tool handle as illustrated in FIG. 6C. In these views, the arrangement of the inner corner surfaces 12, 122, 124 and 126 can be seen. These surfaces, along with side surfaces 128 and 130, are arranged to generally correspond to the corners and the side surfaces of the device, preventing rotation of the device within the handle. The distal facing surface of projection 114 is also visible in this view.

FIGS. 8A, 8B, 8C and 8D are distal end, cut-away, top and proximal end views, respectively, of the plunger of 5B. In these figures, the configuration of the groove 306 can be seen, along with distally facing stop surface 310, which engages with the proximal facing surface of protrusion 114 of the handle, to limit distal movement of the plunger.

Figure 8B:
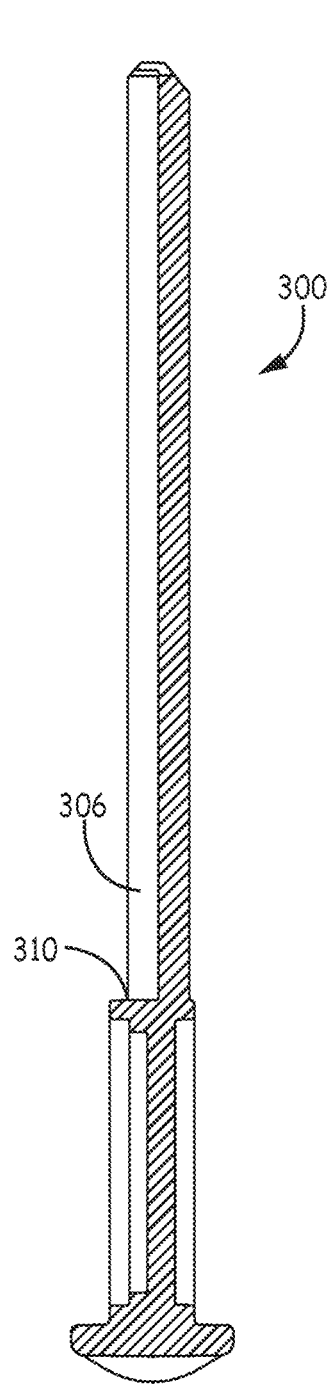
FIGS. 8A, 8B, 8C and 8D are distal end, cut-away, top and proximal end views, respectively, of the plunger of 5B.
Figure 8C:
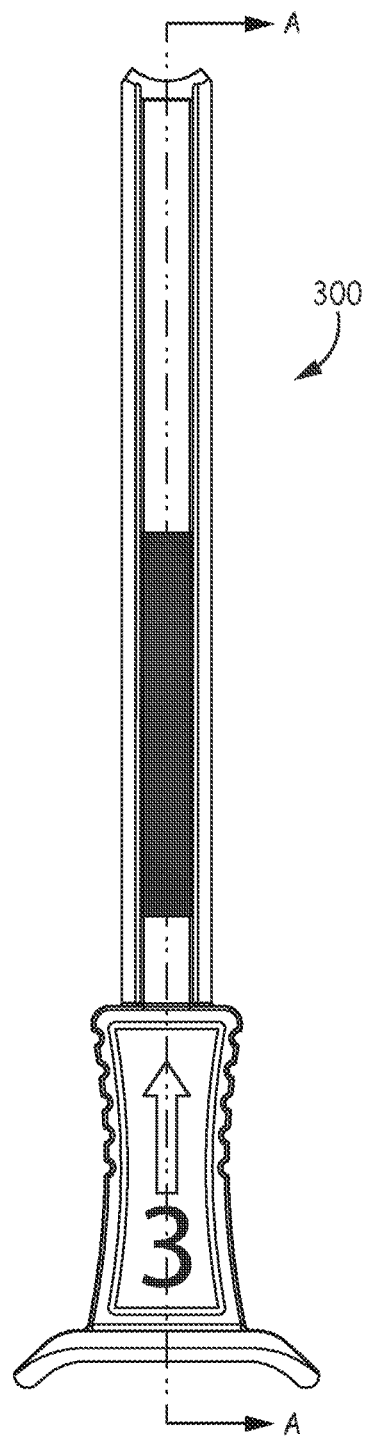
Figure 8A:
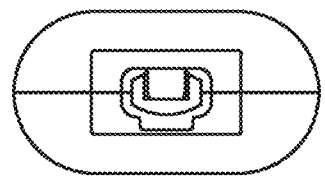
Figure 8D:
Figure 9B:
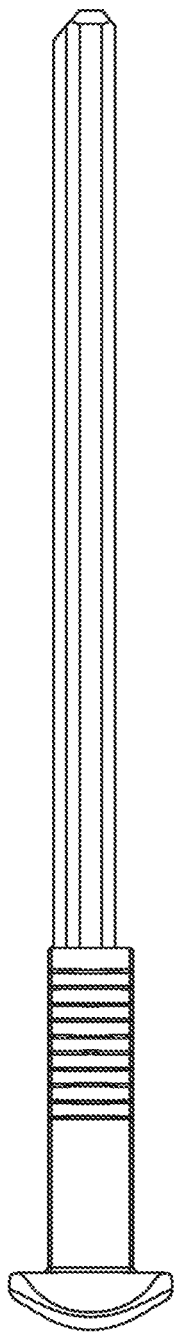
FIGS. 9A, 9B, and 9C are cross sectional, side and bottom views, respectively, of the plunger as illustrated in FIG. 8D.
Figure 9C:
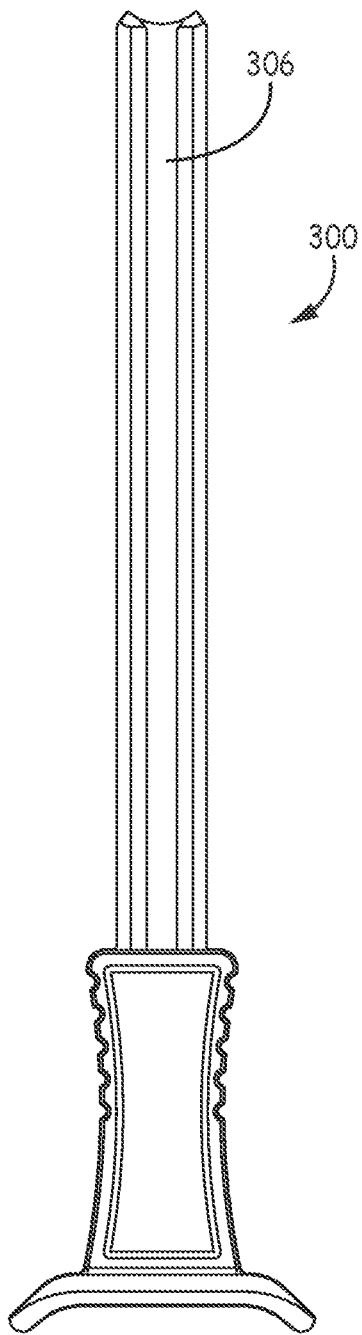
Figure 9A:
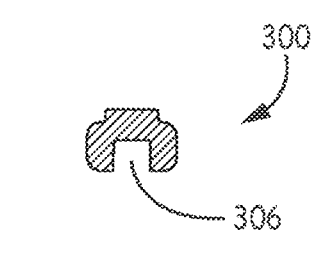

FIGS. 9A, 9B, and 9C are cross sectional, side and bottom views. Respectively, of the plunger as illustrated in FIG. 8D. In these views, the configuration of the groove 306 is visible in more detail.

Figure 10:
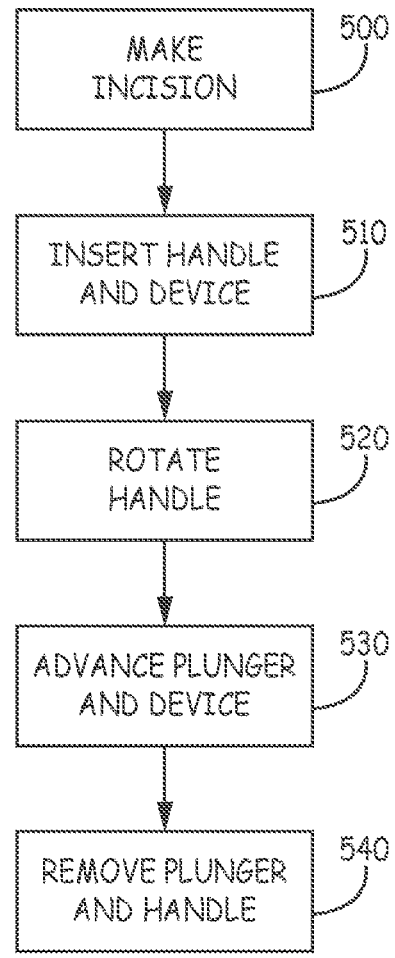

FIG. 10 is a flow chart illustrating a preferred embodiment of an insertion process according to the present invention. At 500, the incision is made using the incision tool. At 510, the handle carrying the device is inserted into the tissue such that the tunneler produces an elongated blunt incision along which the device may be advanced. In this step, the device is located outward of the tunneler relative to the patient's body. At 520 the handle, carrying the device is rotated so that the device is now inward of the tunneler relative to the patient's body. At 530, the device is advanced by the plunger along the handle and along the then inward facing surface of the tunneler subcutaneously into the patient's body. Finally, at 540, the handle and tunneler are removed.

Exemplary embodiments thus described allow for subcutaneous implantation of devices that are minimally invasive. Note that exemplary embodiments may be used in both human and animal patients.

Exemplary embodiments of the present invention being thus described, it will be obvious that the same may be varied in many ways. Such variations are not to be regarded as a departure from the spirit and scope of the exemplary embodiments of the invention, and all such modifications as would be obvious to one skilled in the art are intended to be included within the scope of the invention.

What is claimed is:

1. A method of implanting a medical device in subcutaneous tissue of a patient, the method comprising:
    advancing an implantation tool into an opening in a skin of the patient to create a pocket in the subcutaneous tissue, wherein the implantation tool comprises:
        a first implantation tool portion configured for blunt dissection of the subcutaneous tissue of the patient, the first implantation tool including a first proximal end and a first distal end; and
        a second implantation tool portion including a second proximal end and a second distal end, the second implantation tool portion defining a channel configured to receive the medical device, wherein the second implantation tool portion defines a distal opening of the channel at the second distal end, wherein the first proximal end of the first implantation tool portion adjoins the second distal end of the second implantation tool portion,
    wherein advancing the implantation tool into the opening comprises advancing the first implantation tool portion into the subcutaneous tissue such that the first implantation tool portion performs blunt dissection of the subcutaneous tissue to create the pocket in the subcutaneous tissue, and
    wherein the channel is configured to receive the medical device such that the medical device is outward of the first implantation tool portion relative to a body of the patient when the first implantation tool portion is advanced into the subcutaneous tissue of the patient;
    rotating the implantation tool with the first implantation tool portion within the subcutaneous tissue of the patient so that the medical device is inward of the first implantation tool portion relative to the body of the patient; and
    advancing the medical device out of a distal opening of the channel and through the opening in the skin of the patient while the medical device is inward of the first implantation tool portion relative to the body of the patient to advance the medical device into the pocket in the subcutaneous tissue.

2. The method of claim 1, further comprising creating the opening in the skin of the patient by advancing a blade of an incision tool into the skin of the patient at an angle with a surface of the skin of the patient.

3. The method of claim 2, wherein the incision tool comprises:
    an incision tool handle comprising:
        a proximal end;
        a distal end; and
        a center portion, wherein the center portion curves to the proximal end along a first curve, the first curve defining a first concave curve in a first direction, and wherein the center portion curves to the distal end along a second curve, the second curve defining a second concave curve in a second direction, the second direction being opposite of the first direction; and
    the blade extending from the distal end of the incision tool handle.

4. The method of claim 1, wherein rotating the implantation tool comprises rotating the implantation tool 180 degrees about a longitudinal axis of the implantation tool.

5. The method of claim 1, wherein rotating the implantation tool temporarily enlarges the opening in the skin of the patient.

6. The method of claim 1, wherein the second implantation tool portion includes a logo which reminds a user of the implantation tool to rotate the implantation tool after advancing the first implantation tool portion into the opening.

7. The method of claim 1,
    wherein the implantation tool further comprises a plunger comprising a proximal end and a distal end, wherein plunger is configured to move in the channel, and wherein advancing the medical device out of the distal opening of the channel and through the opening in the skin of the patient comprises:
    distally advancing the plunger along the channel in order to push the medical device out of the channel into the pocket in the subcutaneous tissue along a surface of the first implantation tool portion,
    wherein to push the medical device out of the channel, the distal end of the plunger is configured to push a proximal end of the medical device as the plunger advances into the channel.

8. The method of claim 7,
    wherein the first implantation tool portion defines a projection into the channel, and
    wherein the plunger defines a groove that corresponds to and engages with the projection into the channel.

9. The method of claim 8, wherein the projection and the groove are configured to limit longitudinal movement of the plunger within the channel.

10. The method of claim 7, wherein the distal end of the plunger is movable distally to displace a proximal end of the medical device a distance from the opening in the skin of the patient.

11. The method of claim 7, wherein the distal end of the plunger is tapered.

12. The method of claim 7, wherein the plunger includes a marking which assists a user of the implantation tool in determining that the plunger is in a proper orientation for advancing distally along the channel, and wherein the marking comprises an arrow pointing towards the distal end of the plunger.

13. The method of claim 1, wherein when the medical device is in the pocket in the subcutaneous tissue, an electrode of the medical device faces outwards towards the skin of the patient.

14. The method of claim 1, wherein a proximal opening of the channel is located at the second proximal end of the second implantation tool portion, wherein the distal opening of the channel is located at the second distal end of the second implantation tool portion, and wherein the second implantation tool portion forms one or more additional openings between the second proximal end and the second distal end.

15. The method of claim 14, wherein the second implantation tool portion forms a slot between the second proximal end and the second distal end, wherein advancement of the medical device is observable through the slot.

16. The method of claim 1, wherein the medical device comprises an insertable cardiac monitor (ICM).

17. The method of claim 16, wherein the ICM comprises two electrodes and is configured to monitor an electrocardiogram of the patient via the two electrodes.

18. The method of claim 17, wherein the two electrodes comprise a first electrode adjacent a proximal end of the ICM and a second electrode adjacent a distal end of the ICM.

19. A method of implanting a medical device in subcutaneous tissue of a patient, the method comprising:
    creating an opening in a skin of the patient by advancing a blade of an incision tool into the skin of the patient at an angle with a surface of the skin of the patient;
    advancing an implantation tool into the opening in the skin of the patient to create a pocket in the subcutaneous tissue, wherein the implantation tool comprises:
        a first implantation tool portion; and
        a second implantation tool portion including a proximal end and a distal end, the second implantation tool portion defining a channel configured to receive the medical device, wherein the second implantation tool portion defines a distal opening of the channel at the distal end, wherein the first implantation tool portion adjoins the distal end of the second implantation tool portion,
    wherein advancing the implantation tool into the opening comprises advancing the first implantation tool portion into the subcutaneous tissue such that the first implantation tool portion performs blunt dissection of the subcutaneous tissue to create the pocket in the subcutaneous tissue, and
    wherein the channel is configured to receive the medical device such that the medial device is outward of the first implantation tool portion relative to a body of the patient when the first implantation tool portion is advanced into the subcutaneous tissue of the patient;
rotating the implantation tool with the first implantation tool portion within the subcutaneous tissue of the patient so that the medical device is inward of the first implantation tool portion relative to the body of the patient, wherein rotating the implantation tool temporarily enlarges the pocket in the subcutaneous tissue; and
advancing the medical device out of a distal opening of the channel and through the opening in the skin of the patient while the medical device is inward of the first implantation tool portion relative to the body of the patient to advance the medical device into the pocket in the subcutaneous tissue.

\* \* \* \* \*